United States Patent
Hafezi et al.

(10) Patent No.: US 8,540,633 B2
(45) Date of Patent: Sep. 24, 2013

(54) IDENTIFIER CIRCUITS FOR GENERATING UNIQUE IDENTIFIABLE INDICATORS AND TECHNIQUES FOR PRODUCING SAME

(75) Inventors: Hooman Hafezi, Redwood City, CA (US); Eric Snyder, South San Francisco, CA (US); Benedict Costello, Berkeley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 12/527,403

(22) PCT Filed: Aug. 13, 2009

(86) PCT No.: PCT/US2009/053721
§ 371 (c)(1),
(2), (4) Date: Jul. 27, 2010

(87) PCT Pub. No.: WO2010/019778
PCT Pub. Date: Feb. 18, 2010

(65) Prior Publication Data
US 2010/0298668 A1    Nov. 25, 2010

Related U.S. Application Data

(60) Provisional application No. 61/088,355, filed on Aug. 13, 2008.

(51) Int. Cl.
*A61B 5/07* (2006.01)
(52) U.S. Cl.
USPC ........ 600/302; 600/301; 340/572.1; 429/122; 205/50
(58) Field of Classification Search
USPC ............. 428/544–687, 32.21, 32.22, 35.7, 428/35.8, 35.9, 36.1–36.9, 36.91, 36.92, 428/40.1–42.3, 63, 901, 913, 926–931, 934–941; 205/80, 67, 687, 775–779, 924–928; 977/700–963; 361/271–330, 500–541, 437; 600/300–301; 604/890.1, 891.1, 892.1
See application file for complete search history.

(56) References Cited

U.S. PATENT DOCUMENTS 3,607,788 A   9/1971   Adolph
3,642,008 A   2/1972   Bolduc (Continued)

FOREIGN PATENT DOCUMENTS

EP   0344939   12/1989
EP   1246356   10/2002

(Continued)

OTHER PUBLICATIONS

Jimbo, H. et al in "Gastric-fluid-utilized microbattery for micro medical devices", The Sixth International Workshop on Micro and Nanotechnology for Power Generation and Energy Conversion Applications, Nov. 29-Dec. 1, 2006, Berkeley, U.S.A., p. 97-10.*

(Continued)

*Primary Examiner* — Henry M Johnson, III
*Assistant Examiner* — Marie Archer
(74) *Attorney, Agent, or Firm* — Bozicevic, Field & Francis LLP; Bret E. Field

(57) ABSTRACT

The present invention provides for safe and reliable electronic circuitry that can be employed in ingestible compositions. The ingestible circuitry of the invention includes a solid support; a conductive element; and an electronic component. Each of the support, conductive element and electronic component are fabricated from an ingestible material. The ingestible circuitry finds use in a variety of different applications, including as components of ingestible identifiers, such as may be found in ingestible event markers, e.g., pharma-informatics enabled pharmaceutical compositions.

10 Claims, 8 Drawing Sheets

(56) References Cited

U.S. PATENT DOCUMENTS

| | | | |
|---|---|---|---|
| 3,679,480 A | 7/1972 | Brown et al. | |
| 3,682,160 A | 8/1972 | Murata | |
| 3,719,183 A | 3/1973 | Schwartz | |
| 3,799,802 A * | 3/1974 | Mc Cormack et al. | 205/126 |
| 3,828,766 A | 8/1974 | Krasnow | |
| 3,837,339 A | 9/1974 | Aisenberg et al. | |
| 3,893,111 A | 7/1975 | Cotter | |
| 3,967,202 A | 6/1976 | Batz | |
| 3,989,050 A | 11/1976 | Buchalter | |
| 4,017,856 A | 4/1977 | Wiegand | |
| 4,055,178 A | 10/1977 | Harrigan | |
| 4,077,397 A | 3/1978 | Ellis | |
| 4,077,398 A | 3/1978 | Ellis | |
| 4,082,087 A | 4/1978 | Howson | |
| 4,090,752 A | 5/1978 | Long | |
| 4,106,348 A | 8/1978 | Auphan | |
| 4,129,125 A | 12/1978 | Lester | |
| 4,166,453 A | 9/1979 | McClelland | |
| 4,239,046 A | 12/1980 | Ong | |
| 4,251,795 A | 2/1981 | Shibasaki et al. | |
| 4,269,189 A | 5/1981 | Abraham | |
| 4,331,654 A | 5/1982 | Morris | |
| 4,345,588 A | 8/1982 | Widder et al. | |
| 4,418,697 A | 12/1983 | Tama | |
| 4,425,117 A | 1/1984 | Hugemann et al. | |
| 4,494,950 A | 1/1985 | Fischell | |
| 4,559,950 A | 12/1985 | Vaughan | |
| 4,635,641 A | 1/1987 | Hoffman | |
| 4,654,165 A | 3/1987 | Eisenberg | |
| 4,663,250 A * | 5/1987 | Ong et al. | 429/473 |
| 4,669,479 A | 6/1987 | Dunseath | |
| 4,725,997 A | 2/1988 | Urquhart et al. | |
| 4,763,659 A | 8/1988 | Dunseath | |
| 4,784,162 A | 11/1988 | Ricks | |
| 4,793,825 A | 12/1988 | Benjamin et al. | |
| 4,844,076 A | 7/1989 | Lesho | |
| 4,896,261 A | 1/1990 | Nolan | |
| 4,975,230 A | 12/1990 | Pinkhasov | |
| 4,987,897 A | 1/1991 | Funke | |
| 5,016,634 A | 5/1991 | Vock et al. | |
| 5,079,006 A | 1/1992 | Urquhart | |
| 5,167,626 A | 12/1992 | Casper | |
| 5,176,626 A | 1/1993 | Soehendra | |
| 5,261,402 A | 11/1993 | DiSabito | |
| 5,263,481 A | 11/1993 | Axelgaard et al. | |
| 5,279,607 A | 1/1994 | Schentag et al. | |
| 5,281,287 A | 1/1994 | Lloyd | |
| 5,283,136 A | 2/1994 | Peled et al. | |
| 5,305,745 A | 4/1994 | Zacouto | |
| 5,318,557 A * | 6/1994 | Gross | 604/891.1 |
| 5,394,882 A | 3/1995 | Mawhinney | |
| 5,395,366 A | 3/1995 | D'Andrea et al. | |
| 5,436,091 A * | 7/1995 | Shackle et al. | 429/304 |
| 5,458,141 A | 10/1995 | Neil et al. | |
| 5,485,841 A | 1/1996 | Watkin et al. | |
| 5,596,302 A | 1/1997 | Mastrocola et al. | |
| 5,600,548 A | 2/1997 | Nguyen et al. | |
| 5,634,468 A | 6/1997 | Platt | |
| 5,645,063 A | 7/1997 | Straka et al. | |
| 5,738,708 A | 4/1998 | Peachey et al. | |
| 5,740,811 A | 4/1998 | Hedberg | |
| 5,757,326 A | 5/1998 | Koyama et al. | |
| 5,792,048 A | 8/1998 | Schaefer | |
| 5,796,038 A * | 8/1998 | Manteghi | 174/526 |
| 5,802,467 A | 9/1998 | Salazar | |
| 5,833,716 A | 11/1998 | Bar-Or | |
| 5,845,265 A | 12/1998 | Woolston | |
| 5,862,803 A | 1/1999 | Besson | |
| 5,868,136 A | 2/1999 | Fox | |
| 5,925,030 A | 7/1999 | Gross et al. | |
| 5,957,854 A | 9/1999 | Besson | |
| 5,963,132 A | 10/1999 | Yoakum et al. | |
| 5,974,124 A | 10/1999 | Schlueter, Jr. et al. | |
| 5,999,846 A | 12/1999 | Pardey et al. | |
| 6,038,464 A | 3/2000 | Axelgaard et al. | |
| 6,042,710 A | 3/2000 | Dubrow | |
| 6,047,203 A | 4/2000 | Sackner | |
| 6,076,016 A | 6/2000 | Feierbach et al. | |
| 6,081,734 A | 6/2000 | Batz | |
| 6,095,985 A | 8/2000 | Raymond et al. | |
| 6,122,351 A | 9/2000 | Schlueter, Jr. et al. | |
| 6,141,592 A | 10/2000 | Pauly | |
| 6,156,343 A * | 12/2000 | Morita et al. | 424/474 |
| 6,200,265 B1 | 3/2001 | Walsh et al. | |
| 6,206,702 B1 | 3/2001 | Hayden et al. | |
| 6,217,744 B1 | 4/2001 | Crosby | |
| 6,231,593 B1 | 5/2001 | Meserol | |
| 6,245,057 B1 | 6/2001 | Sieben et al. | |
| 6,269,058 B1 | 7/2001 | Yamanoi et al. | |
| 6,285,897 B1 | 9/2001 | Kilcoyne et al. | |
| 6,287,252 B1 | 9/2001 | Lugo | |
| 6,288,629 B1 | 9/2001 | Cofino et al. | |
| 6,289,238 B1 | 9/2001 | Besson | |
| 6,315,719 B1 | 11/2001 | Rode et al. | |
| 6,358,202 B1 | 3/2002 | Arent | |
| 6,364,834 B1 | 4/2002 | Reuss | |
| 6,366,206 B1 | 4/2002 | Ishikawa et al. | |
| 6,371,927 B1 | 4/2002 | Brune | |
| 6,374,670 B1 | 4/2002 | Spelman | |
| 6,380,858 B1 | 4/2002 | Yarin et al. | |
| 6,394,997 B1 | 5/2002 | Lemelson | |
| 6,426,863 B1 | 7/2002 | Munshi | |
| 6,432,292 B1 | 8/2002 | Pinto et al. | |
| 6,440,069 B1 | 8/2002 | Raymond et al. | |
| 6,441,747 B1 | 8/2002 | Khair | |
| 6,453,199 B1 | 9/2002 | Kobozev | |
| 6,477,424 B1 | 11/2002 | Thompson et al. | |
| 6,496,705 B1 | 12/2002 | Ng et al. | |
| 6,526,315 B1 | 2/2003 | Inagawa | |
| 6,531,026 B1 * | 3/2003 | Takeichi et al. | 156/282 |
| 6,544,174 B2 | 4/2003 | West | |
| 6,564,079 B1 | 5/2003 | Cory | |
| 6,577,893 B1 | 6/2003 | Besson | |
| 6,579,231 B1 | 6/2003 | Phipps | |
| 6,609,018 B2 | 8/2003 | Cory | |
| 6,612,984 B1 | 9/2003 | Kerr | |
| 6,632,175 B1 | 10/2003 | Marshall | |
| 6,632,216 B2 | 10/2003 | Houzego et al. | |
| 6,643,541 B2 | 11/2003 | Mok et al. | |
| 6,654,638 B1 | 11/2003 | Sweeney | |
| 6,663,846 B1 | 12/2003 | McCombs | |
| 6,673,474 B2 | 1/2004 | Yamamoto | |
| 6,680,923 B1 | 1/2004 | Leon | |
| 6,689,117 B2 | 2/2004 | Sweeney et al. | |
| 6,694,161 B2 | 2/2004 | Mehrotra | |
| 6,704,602 B2 | 3/2004 | Berg et al. | |
| 6,720,923 B1 | 4/2004 | Hayward et al. | |
| 6,738,671 B2 | 5/2004 | Christophersom et al. | |
| 6,740,033 B1 | 5/2004 | Olejniczak et al. | |
| 6,745,082 B2 | 6/2004 | Axelgaard et al. | |
| 6,755,783 B2 | 6/2004 | Cosentino | |
| 6,757,523 B2 | 6/2004 | Fry | |
| 6,800,060 B2 | 10/2004 | Marshall | |
| 6,801,137 B2 | 10/2004 | Eggers et al. | |
| 6,822,554 B2 | 11/2004 | Vrijens et al. | |
| 6,836,862 B1 | 12/2004 | Erekson et al. | |
| 6,839,659 B2 | 1/2005 | Tarassenko et al. | |
| 6,840,904 B2 | 1/2005 | Goldberg | |
| 6,842,636 B2 | 1/2005 | Perrault | |
| 6,845,272 B1 | 1/2005 | Thomsen | |
| 6,864,780 B2 | 3/2005 | Doi | |
| 6,879,810 B2 | 4/2005 | Bouet | |
| 6,909,878 B2 | 6/2005 | Haller | |
| 6,922,592 B2 | 7/2005 | Thompson et al. | |
| 6,928,370 B2 | 8/2005 | Anuzis et al. | |
| 6,929,636 B1 | 8/2005 | von Alten | |
| 6,937,150 B2 | 8/2005 | Medema | |
| 6,942,616 B2 | 9/2005 | Kerr | |
| 6,951,536 B2 | 10/2005 | Yokoi | |
| 6,957,107 B2 | 10/2005 | Rogers et al. | |
| 6,968,153 B1 | 11/2005 | Heinonen | |
| 6,977,511 B2 * | 12/2005 | Patel et al. | 324/661 |
| 6,987,965 B2 | 1/2006 | Ng et al. | |
| 6,990,082 B1 | 1/2006 | Zehavi et al. | |

| Patent | Type | Date | Name |
|---|---|---|---|
| 7,002,476 | B2 | 2/2006 | Rapchak |
| 7,004,395 | B2 | 2/2006 | Koenck |
| 7,009,634 | B2 | 3/2006 | Iddan et al. |
| 7,009,946 | B1 | 3/2006 | Kardach |
| 7,013,162 | B2 | 3/2006 | Gorsuch |
| 7,016,648 | B2 | 3/2006 | Haller |
| 7,020,508 | B2 | 3/2006 | Stivoric |
| 7,024,248 | B2 | 4/2006 | Penner et al. |
| 7,031,745 | B2 | 4/2006 | Shen |
| 7,031,857 | B2 | 4/2006 | Tarassenko et al. |
| 7,039,453 | B2 | 5/2006 | Mullick |
| 7,046,649 | B2 | 5/2006 | Awater et al. |
| 7,118,531 | B2 | 10/2006 | Krill |
| 7,127,300 | B2 | 10/2006 | Mazar et al. |
| 7,146,228 | B2 | 12/2006 | Nielsen |
| 7,146,449 | B2 | 12/2006 | Do et al. |
| 7,149,581 | B2 | 12/2006 | Goedeke et al. |
| 7,154,071 | B2 | 12/2006 | Sattler et al. |
| 7,155,232 | B2 | 12/2006 | Godfrey et al. |
| 7,160,258 | B2 | 1/2007 | Imran |
| 7,164,942 | B2 | 1/2007 | Avrahami |
| 7,171,166 | B2 | 1/2007 | Ng et al. |
| 7,171,177 | B2 | 1/2007 | Park et al. |
| 7,171,259 | B2 | 1/2007 | Rytky |
| 7,176,784 | B2 | 2/2007 | Gilbert et al. |
| 7,187,960 | B2 | 3/2007 | Abreu |
| 7,188,767 | B2 | 3/2007 | Penuela |
| 7,194,038 | B1 | 3/2007 | Inkinen |
| 7,206,630 | B1 | 4/2007 | Tarler |
| 7,209,790 | B2 | 4/2007 | Thompson et al. |
| 7,215,660 | B2 | 5/2007 | Perlman |
| 7,215,991 | B2 | 5/2007 | Besson |
| 7,218,967 | B2 | 5/2007 | Bergelson |
| 7,231,451 | B2 | 6/2007 | Law |
| 7,243,118 | B2 | 7/2007 | Lou |
| 7,246,521 | B2 | 7/2007 | Kim |
| 7,249,212 | B2 | 7/2007 | Do |
| 7,252,792 | B2 | 8/2007 | Perrault |
| 7,253,716 | B2 | 8/2007 | Lovoi et al. |
| 7,261,690 | B2 | 8/2007 | Teller |
| 7,270,633 | B1 | 9/2007 | Goscha |
| 7,273,454 | B2 | 9/2007 | Raymond et al. |
| 7,289,855 | B2 | 10/2007 | Nghiem |
| 7,291,497 | B2 | 11/2007 | Holmes |
| 7,292,139 | B2 | 11/2007 | Mazar et al. |
| 7,294,105 | B1 | 11/2007 | Islam |
| 7,313,163 | B2 | 12/2007 | Liu |
| 7,317,378 | B2 | 1/2008 | Jarvis et al. |
| 7,318,808 | B2 | 1/2008 | Tarassenko et al. |
| 7,336,929 | B2 | 2/2008 | Yasuda |
| 7,342,895 | B2 | 3/2008 | Serpa |
| 7,346,380 | B2 | 3/2008 | Axelgaard et al. |
| 7,349,722 | B2 | 3/2008 | Witkowski et al. |
| 7,352,998 | B2 | 4/2008 | Palin |
| 7,353,258 | B2 | 4/2008 | Washburn |
| 7,357,891 | B2 * | 4/2008 | Yang et al. ............... 264/211.12 |
| 7,359,674 | B2 | 4/2008 | Markki |
| 7,366,558 | B2 | 4/2008 | Virtanen et al. |
| 7,368,191 | B2 | 5/2008 | Andelman et al. |
| 7,373,196 | B2 | 5/2008 | Ryu et al. |
| 7,375,739 | B2 | 5/2008 | Robbins |
| 7,376,435 | B2 | 5/2008 | McGowan |
| 7,382,263 | B2 | 6/2008 | Danowski et al. |
| 7,387,607 | B2 | 6/2008 | Holt |
| 7,388,903 | B2 | 6/2008 | Godfrey et al. |
| 7,389,088 | B2 | 6/2008 | Kim |
| 7,392,015 | B1 | 6/2008 | Farlow |
| 7,395,106 | B2 | 7/2008 | Ryu et al. |
| 7,396,330 | B2 | 7/2008 | Banet |
| 7,404,968 | B2 * | 7/2008 | Abrams et al. ................. 424/443 |
| 7,413,544 | B2 | 8/2008 | Kerr |
| 7,414,534 | B1 | 8/2008 | Kroll et al. |
| 7,414,543 | B2 | 8/2008 | Rye et al. |
| 7,415,242 | B1 | 8/2008 | Ngan |
| 7,424,268 | B2 | 9/2008 | Diener |
| 7,424,319 | B2 | 9/2008 | Muehlsteff |
| 7,427,266 | B2 | 9/2008 | Ayer et al. |
| 7,471,665 | B2 | 12/2008 | Perlman |
| 7,499,674 | B2 | 3/2009 | Salokannel |
| 7,510,121 | B2 | 3/2009 | Koenck |
| 7,512,448 | B2 | 3/2009 | Malick |
| 7,515,043 | B2 | 4/2009 | Welch |
| 7,519,416 | B2 | 4/2009 | Sula et al. |
| 7,523,756 | B2 | 4/2009 | Minai |
| 7,525,426 | B2 | 4/2009 | Edelstein |
| 7,539,533 | B2 | 5/2009 | Tran |
| 7,542,878 | B2 | 6/2009 | Nanikashvili |
| 7,551,590 | B2 | 6/2009 | Haller |
| 7,554,452 | B2 | 6/2009 | Cole |
| 7,575,005 | B2 | 8/2009 | Mumford |
| 7,616,111 | B2 | 11/2009 | Covannon |
| 7,617,001 | B2 | 11/2009 | Penner et al. |
| 7,639,473 | B2 * | 12/2009 | Hsu et al. ..................... 361/260 |
| 7,640,802 | B2 | 1/2010 | King et al. |
| 7,647,112 | B2 | 1/2010 | Tracey |
| 7,647,185 | B2 | 1/2010 | Tarassenko et al. |
| 7,653,031 | B2 | 1/2010 | Godfrey et al. |
| 7,672,714 | B2 | 3/2010 | Kuo |
| 7,673,679 | B2 | 3/2010 | Harrison et al. |
| 7,678,043 | B2 | 3/2010 | Gilad |
| 7,697,994 | B2 | 4/2010 | VanDanacker et al. |
| 7,720,036 | B2 | 5/2010 | Sadri |
| 7,729,776 | B2 | 6/2010 | Von Arx et al. |
| 7,733,224 | B2 | 6/2010 | Tran |
| 7,736,318 | B2 | 6/2010 | Costentino |
| 7,756,587 | B2 | 7/2010 | Penner et al. |
| 7,796,043 | B2 | 9/2010 | Euliano et al. |
| 7,809,399 | B2 | 10/2010 | Lu |
| 7,844,341 | B2 | 11/2010 | Von Arx et al. |
| 2001/0027331 | A1 | 10/2001 | Thompson |
| 2001/0044588 | A1 | 11/2001 | Mault |
| 2001/0051766 | A1 | 12/2001 | Gazdzinski et al. |
| 2002/0002326 | A1 | 1/2002 | Causey, III |
| 2002/0026111 | A1 | 2/2002 | Ackerman |
| 2002/0032385 | A1 | 3/2002 | Raymond et al. |
| 2002/0040278 | A1 | 4/2002 | Anuzis et al. |
| 2002/0077620 | A1 | 6/2002 | Sweeney et al. |
| 2002/0132226 | A1 | 9/2002 | Nair |
| 2002/0193669 | A1 | 12/2002 | Glukhovsky |
| 2003/0017826 | A1 | 1/2003 | Fishman |
| 2003/0023150 | A1 | 1/2003 | Yokoi et al. |
| 2003/0028226 | A1 | 2/2003 | Thompson |
| 2003/0062551 | A1 * | 4/2003 | Chen ............................ 257/211 |
| 2003/0065536 | A1 | 4/2003 | Hansen |
| 2003/0076179 | A1 | 4/2003 | Branch et al. |
| 2003/0083559 | A1 | 5/2003 | Thompson |
| 2003/0126593 | A1 | 7/2003 | Mault |
| 2003/0130714 | A1 | 7/2003 | Nielsen et al. |
| 2003/0135128 | A1 | 7/2003 | Suffin et al. |
| 2003/0135392 | A1 | 7/2003 | Vrijens et al. |
| 2003/0152622 | A1 | 8/2003 | Louie-Helm et al. |
| 2003/0158466 | A1 | 8/2003 | Lynn et al. |
| 2003/0158756 | A1 | 8/2003 | Abramson |
| 2003/0162556 | A1 | 8/2003 | Libes |
| 2003/0167000 | A1 | 9/2003 | Mullick et al. |
| 2003/0171791 | A1 | 9/2003 | KenKnight |
| 2003/0171898 | A1 | 9/2003 | Tarassenko et al. |
| 2003/0181788 | A1 | 9/2003 | Yokoi et al. |
| 2003/0185286 | A1 | 10/2003 | Yuen |
| 2003/0187337 | A1 | 10/2003 | Tarassenko et al. |
| 2003/0187338 | A1 | 10/2003 | Say et al. |
| 2003/0195403 | A1 | 10/2003 | Berner et al. |
| 2003/0213495 | A1 | 11/2003 | Fujita et al. |
| 2003/0214579 | A1 | 11/2003 | Iddan |
| 2003/0216622 | A1 | 11/2003 | Meron et al. |
| 2003/0216625 | A1 | 11/2003 | Phipps |
| 2003/0216666 | A1 | 11/2003 | Ericson et al. |
| 2003/0216729 | A1 | 11/2003 | Marchitto |
| 2004/0008123 | A1 | 1/2004 | Carrender et al. |
| 2004/0018476 | A1 | 1/2004 | LaDue |
| 2004/0034295 | A1 | 2/2004 | Salganicoff |
| 2004/0049245 | A1 | 3/2004 | Gass |
| 2004/0073095 | A1 | 4/2004 | Causey et al. |
| 2004/0073454 | A1 | 4/2004 | Urquhart et al. |
| 2004/0077995 | A1 | 4/2004 | Ferek-Petric |
| 2004/0082982 | A1 | 4/2004 | Gord et al. |
| 2004/0087839 | A1 | 5/2004 | Raymond et al. |
| 2004/0092801 | A1 | 5/2004 | Drakulic |

| | | |
|---|---|---|
| 2004/0106859 A1 | 6/2004 | Say et al. |
| 2004/0115517 A1 | 6/2004 | Fukuda et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0208251 A1* | 9/2005 | Aisenbrey .................... 428/40.1 |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0280227 A1 | 12/2006 | Pinkney |
| 2006/0282001 A1 | 12/2006 | Noel |
| 2006/0289640 A1* | 12/2006 | Mercure et al. ................ 235/435 |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowski |
| 2008/0020037 A1 | 1/2008 | Robertson |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0039700 A1 | 2/2008 | Drinan et al. |
| 2008/0046038 A1 | 2/2008 | Hill |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1* | 5/2008 | Ferren et al. ................ 604/95.01 |
| 2008/0114224 A1 | 5/2008 | Bandy et al. |

| | | |
|---|---|---|
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1* | 8/2008 | Belsky et al. .............. 604/890.1 |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1* | 1/2009 | Sakama et al. ............. 340/572.1 |
| 2009/0009332 A1 | 1/2009 | Nunez et al. |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076343 A1 | 3/2009 | James |
| 2009/0082645 A1 | 3/2009 | Hafezi |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0010330 A1 | 1/2010 | Rankers |
| 2010/0049006 A1 | 2/2010 | Magar |
| 2010/0049012 A1* | 2/2010 | Dijksman et al. ............. 600/302 |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0099967 A1 | 4/2010 | Say et al. |
| 2010/0099968 A1 | 4/2010 | Say et al. |
| 2010/0099969 A1 | 4/2010 | Say et al. |

| | | | |
|---|---|---|---|
| 2010/0100077 A1 | 4/2010 | Rush | |
| 2010/0100078 A1 | 4/2010 | Say et al. | |
| 2010/0106001 A1 | 4/2010 | Say et al. | |
| 2010/0118853 A1 | 5/2010 | Godfrey | |
| 2010/0139672 A1 | 6/2010 | Kroll et al. | |
| 2010/0168659 A1 | 7/2010 | Say et al. | |
| 2010/0179398 A1 | 7/2010 | Say et al. | |
| 2010/0185055 A1 | 7/2010 | Robertson | |
| 2010/0191073 A1 | 7/2010 | Tarassenko et al. | |
| 2010/0210299 A1 | 8/2010 | Gorbachov | |
| 2010/0222652 A1 | 9/2010 | Cho | |
| 2010/0228113 A1 | 9/2010 | Solosko | |
| 2010/0234706 A1 | 9/2010 | Gilland | |
| 2010/0234715 A1 | 9/2010 | Shin | |
| 2010/0234914 A1 | 9/2010 | Shen | |
| 2010/0239616 A1 | 9/2010 | Hafezi et al. | |
| 2010/0245091 A1 | 9/2010 | Singh | |
| 2010/0249881 A1 | 9/2010 | Corndorf | |
| 2010/0256461 A1 | 10/2010 | Mohamedali | |
| 2010/0259543 A1 | 10/2010 | Tarassenko et al. | |
| 2010/0268048 A1 | 10/2010 | Say et al. | |
| 2010/0268049 A1 | 10/2010 | Say et al. | |
| 2010/0268050 A1 | 10/2010 | Say et al. | |
| 2010/0274111 A1 | 10/2010 | Say et al. | |
| 2010/0280345 A1 | 11/2010 | Say et al. | |
| 2010/0280346 A1 | 11/2010 | Say et al. | |
| 2010/0295694 A1 | 11/2010 | Kauffman et al. | |
| 2010/0298668 A1 | 11/2010 | Hafezi et al. | |
| 2010/0298730 A1 | 11/2010 | Tarassenko et al. | |
| 2010/0312188 A1 | 12/2010 | Robertson et al. | |
| 2010/0312580 A1 | 12/2010 | Tarassenko et al. | |
| 2011/0009715 A1 | 1/2011 | O'Reilly et al. | |
| 2011/0054265 A1 | 3/2011 | Hafezi et al. | |
| 2011/0065983 A1 | 3/2011 | Hafezi et al. | |
| 2011/0105864 A1 | 5/2011 | Robertson et al. | |

FOREIGN PATENT DOCUMENTS

| | | |
|---|---|---|
| EP | 1534054 | 5/2005 |
| EP | 1702553 | 9/2006 |
| EP | 1789128 | 5/2007 |
| EP | 2143369 | 1/2010 |
| JP | 61072712 | 4/1986 |
| JP | 05-228128 | 9/1993 |
| JP | 2000-506410 | 5/2000 |
| JP | 2002263185 | 9/2002 |
| JP | 2005073886 | 3/2005 |
| JP | 2005-304880 | 4/2005 |
| JP | 2006006377 | 1/2006 |
| JP | 2006509574 | 3/2006 |
| JP | 2007-313340 | 12/2007 |
| KR | 2006077523 | 7/2006 |
| WO | 8802237 | 4/1988 |
| WO | WO8802237 | 4/1988 |
| WO | WO9308734 | 5/1993 |
| WO | WO9319667 | 10/1993 |
| WO | WO9739963 | 10/1997 |
| WO | WO9843537 | 10/1998 |
| WO | WO9959465 | 11/1999 |
| WO | WO0033246 | 6/2000 |
| WO | WO0100085 | 1/2001 |
| WO | 01/47466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO2004014225 | 2/2004 |
| WO | WO2004039256 | 5/2004 |
| WO | WO2004066834 | 8/2004 |
| WO | WO2004066903 | 8/2004 |
| WO | WO2004068881 | 8/2004 |
| WO | WO2004109316 | 12/2004 |
| WO | WO2005011237 | 2/2005 |
| WO | 2005/020023 | 3/2005 |
| WO | WO2005024687 | 3/2005 |
| WO | WO2005047837 | 5/2005 |
| WO | WO2005051166 | 6/2005 |
| WO | WO2005110238 | 11/2005 |
| WO | WO2006027586 | 3/2006 |
| WO | 2006/055892 | 5/2006 |
| WO | 2006/055956 | 5/2006 |
| WO | WO2006075016 | 7/2006 |
| WO | WO2006100620 | 9/2006 |
| WO | 2006/104843 | 10/2006 |
| WO | 2006/116718 | 11/2006 |
| WO | 2006/127355 | 11/2006 |
| WO | 2007/001724 | 1/2007 |
| WO | 2007/001742 | 1/2007 |
| WO | 2007/013952 | 2/2007 |
| WO | 2007/014084 | 2/2007 |
| WO | 2007/021496 | 2/2007 |
| WO | WO2007014527 | 2/2007 |
| WO | 2007/027660 | 3/2007 |
| WO | 2007/028035 | 3/2007 |
| WO | WO2007028035 | 3/2007 |
| WO | 2007036741 | 4/2007 |
| WO | 2007036746 | 4/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | 2007130491 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | 2007/149546 | 12/2007 |
| WO | WO2007143535 | 12/2007 |
| WO | 2008/008281 | 1/2008 |
| WO | WO2008030482 | 3/2008 |
| WO | 2008/052136 | 5/2008 |
| WO | 2008/063626 | 5/2008 |
| WO | 2008/066617 | 6/2008 |
| WO | WO2008076464 | 6/2008 |
| WO | WO2008089232 | 7/2008 |
| WO | WO2008091683 | 7/2008 |
| WO | 2008/095183 | 8/2008 |
| WO | 2008/101107 | 8/2008 |
| WO | WO2008097652 | 8/2008 |
| WO | 2008/112577 | 9/2008 |
| WO | 2008/112578 | 9/2008 |
| WO | 2008120156 | 10/2008 |
| WO | WO2008133394 | 11/2008 |
| WO | WO2008134185 | 11/2008 |
| WO | 2009001108 | 12/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | 2010019778 | 2/2010 |
| WO | 2010057049 | 5/2010 |
| WO | WO2010080765 | 7/2010 |
| WO | WO2010080843 | 7/2010 |
| WO | WO2010107563 | 9/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |

OTHER PUBLICATIONS

Soper, S. A. et al in "Bio-Mems Technologies and Applications", Chapter 12, "MEMS for Drug Delivery", p. 325-346.*

Li, P-Y, et al in "An electrochemical intraocular drug delivery device", Sensors and Actuators A 143 (2008) p. 41-48.*

Tierney, M. J., et al in "Electroreleasing Composite Membranes for Delivery of Insulin and other Biomacromolecules", J. Electrochem. Soc., vol. 137, No. 6, Jun. 1990, p. 2005-2006.*

Coury, L. "Conductance Measurement Part 1: Theory", Current Separations, 18:3 (1999), p. 91-96.*

Watson, S. J. et al in "Determination of the relationship between the pH and conductivity of gastric juice", Physiol. Meas. 17 (1996) p. 21-27.*

Soper, S. A. et al in "Bio-Mems Technologies and Applications", Chapter 12, "MEMS for Drug Delivery", p. 325-346. 2006.*

Heydari et al., "Analysis of the PLL jitter due to power/ground and substrate noise"; IEEE Transactions on Circuits and Systems (2004) 51(12): 2404-16.

Philips Respironics (http/minimitter.com/products.cfm) Products, Noninvasive Technology to Help Your Studies Succeed. 510(k) Permanent Notification for Vital Sense. Apr. 22, 2004.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Yang et al., "Fast-switching frequency synthesizer with a discriminator-aided phase detector" IEEE Journal of Solid-State Circuits (2000) 35(10): 1445-52.

"Smartlife awarded patent for knitted transducer" Innovation in Textiles News: http://www.innovationintextiles.com/articles/208.php; 2pp. (2009).

Description of ePatch Technology Platform for ECG and EMG, located it http://www.madebydelta.com/imported/images/DELTA_Web/documents/ME/ePatch_ECG_EMG.pdf, Dated Sep. 2, 2010.

Bohidar et al., "Dielectric Behavior of Gelatin Solutions and Gels" Colloid Polym Sci (1998) 276:81-86.

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.

Ferguson et al., "Dialectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Given Imaging, "Agile Patency Brochure" (2006) http://www.inclino.no/documents/AgilePatencyBrochure_Global_GMB-0118-01.pdf; 4pp.

ISFET—Ion Sensitive Field-Effect Transistor; Microsens S.A. pdf document. First in Office Action dated Jun. 13, 2011 for U.S. Appl. No. 12/238,345; 4pp.

INTROMEDIC, MicroCam Innovative Capsule Endoscope Pamphlet. (2006) 8 pp (http://www.intromedic.com/en/product/productinfo.asp).

Kamada K., "Electrophoretic deposition assisted by soluble anode" Materials Letters 57 (2003) 2348-2351.

NPL_AntennaBasics.pdf, Radio Antennae, http://www.erikdeman.de/html/sail018h.htm; (2008) 3pp.

O'Brien et al., "The Production and Characterization of Chemically Reactive Porous Coatings of Zirconium Via Unbalanced Magnetron Sputtering" Surface and Coatings Technology (1996) 86-87; 200-206.

Roulstone, et al., "Studies on Polymer Latex Films: I. A study of latex film morphology" Polymer International 24 (1991) pp. 87-94.

Shin et al., "A Simple Route to Metal Nanodots and Nanoporous Metal Films"; Nano Letters, vol. 2, No. 9 (2002) pp. 933-936.

Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010.

"The SmartPill Wireless Motility Capsule" Smartpill, The Measure of GI Health; (2010) http://www.smartpillcorp.com/index.cfm?pagepath=Products/The_SmartPill_Capsule&id=17814.

Soper, S.A. et al. "Bio-Mems Technologies and Applications", Chapter 12, "MEMS for Drug Delivery", p. 325-346 (2007).

U.S. Appl. No. 12/238,345 filed Sep. 25, 2008, Hooman et al., Non-Final Office Action mailed Jun. 13, 2011 22pp.

Walkey, "MOSFET Structure and Processing"; 97.398* Physical Electronics Lecture 20; First in Office Action dated Jun. 13, 2011 for U.S. Appl. No. 12/238,345; 24 pp.

Wongmanerod et al., "Determination of pore size distribution and surface area of thin porous silicon layers by spectroscopic ellipsometry" Applied Surface Science 172 (2001) 117-125.

ISFET—Ion Sensitive Field-Effect Transistor; Microsens S.A. pdf document. pp. 1-4.

Walkey, "MOSFET Struture and Processing"; 97.398* Physical Electronics Lecture 20; pp. 1-24.

MacKay et al., Radio telemetering from within the body: Inside information is revealed by tiny transmitters that can be swallowed or implanted in man or animal. Science 1961;134(3486):1196-1202.

MacKay et al,. Endoradiosonde. Nature 1957;179(4572):1239-40, 179.

Zworkin, A 'radio pill.' Nature 1957;179:898.

Yao et al., Low Power Digital Communication in Implantable Devices Using Volume Conduction of Biological Tissues. Proceedings of the 28th IEEE, EMBC Annual International Conference (Aug. 30-Sep. 3, 2006); New York, USA.

McKenzie et al., Validation of a new telemetric core temperature monitor. J. Therm. Biol. 2004;29(7-8):605-11.

Tatbul et al., Confidence-based data management for personal area sensor networks. ACM International Conference Proceeding Series 2004;72.

Zimmerman, Personal Area Networks: Near-field intrabody communication. IBM Systems Journal 1996;35 (3-4):609-17.

Mini Mitter Co, Inc. 510(k) Premarket Notification Mini-Logger for Diagnostic Spirometer. Sep. 21, 1999.

Mini Mitter Co, Inc. 510(k) Premarket Notification for VitalSense. Apr. 22, 2004.

Mini Mitter Co, Inc. Actiheart. Traditional 510(k) Summary. Sep. 27, 2005.

Mini Mitter Co, Inc. VitalSense- Wireless Vital Signs Monitoring. Temperatures.com Mar. 31, 2009.

Mini Mitter Co, Inc. Noninvasive technology to help your studies succeed. Mini Mitter.com Mar. 31, 2009.

Barrie, Heidelberg pH capsule gastric analysis. Textbook of Natural Medicine, 1992, Pizzomo, Murray & Barrie.

Carlson et al., Evaluation of a non-invasive respiratory monitoring system for sleeping subjects. Physiological Measurement 1999;20(1):53.

Mojaverian et al., Estimation of gastric residence time of the Heidelberg capsule in humans: effect of varying food composition. Gastroenterology 1985;89(2):392-7.

Xiaoming et al., A telemedicine system for wireless home healthcare based on bluetooth and the internet. Telemedicine Journal and e-health 2004;10(S2):S110-6.

Arshak et al., A Review and Adaptation of Methods of Object Tracking to Telemetry Capsules IC-Med (2007) vol. 1, No. 1, Issue 1, pp. 35 of 46.

"ASGE Technology Status Evaluation Report: wireless capsule endoscopy" American Soc. For Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Brock, "Smart Medicine: The Application of Auto-ID Technology to Healthcare" Auto-ID Labs (2002) http://www.autoidlabs.org/uploads/media/MIT-AUTOID-WH-010.pdf.

Delvaux et al., "Capsule endoscopy: Technique and indications" Clinical Gastoenterology (2008) vol. 22, Issue 5, pp. 813-837.

Fawaz et al., "Enhanced Telemetry System using CP-QPSK Band-Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.

Given Imaging, "Agile Patency Brochure" http://www.inclino.no/documents/AgilePatencyBrochure_Global_GMB-0118-01.pdf;(N.D.) 4pp.

Gonzalez-Guillaumin et al., "Ingestible capsule for impedance and pH monitoring in the esophagus" IEEE Trans Biomed Eng. (2007) 54(12: 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Melanson, "Walkers swallow RFID pills for science" Engadget (2008); http://www.engadget.com/2008/07/29/walkers-swallow-rfid-pills-for-science/.

"New 'smart pill' to track adherence" E-Health-Insider (2010) http://www.e-health-insider.com/news/5910/new_'smart_pill'_monitors_medicines.

"RFID "pill" monitors marchers" RFID News (2008) http://www.rfidnews.org/2008/07/23/rfid-pill-monitors-marchers/.

"SensiVida minimally invasive clinical systems" Investor Presentation (Oct. 2009) 28pp; http://www.sensividamedtech.com/SensiVidaGeneralOctober09.pdf.

Shrivas et al., "A New Platform for Bioelectronics-Electronic Pill", Cummins College, N.D.; http://www.cumminscollege.org/downloads/electronics_and_telecommunication/Newsletters/Current%20Newsletters.pdf.

"The SmartPill Wireless Motility Capsule" SMARTPILL, The Measure of GI Health; http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Swedberg, "University Team Sees Ingestible RFID Tag as a Boon to Clinical Trials" RFID Journal (Apr. 27, 2010); http://www.rfidjournal.com/article/view/7560/1.

University of Florida News "Rx for health: Engineers design pill that signals it has been swallowed" (2010) 2pp.; http://news.ufl.edu/2010/03/31/antenna-pill-2/.

Gilson, D.R. "Molecular dynamics simulation of dipole interactions", Department of Physics, Hull University, Dec. 2002, p. 1-43.

Li, P-Y, et al. "An electrochemical intraocular drug delivery device", Sensors and Actuators A 143 (2008) p. 41-48.

NPL_AntennaBasics.pdf, p. 1-3, Date: Jan. 11, 2008.

Santini, J.T. et al, "Microchips as controlled drug delivery-devices", Agnew. Chem. Int. Ed. 2000, vol. 39, p. 2396-2407.

Shawgo, R.S. et al. "BioMEMS from drug delivery", Current Opinion in Solid State and Material Science 6 (2002), p. 329-334.

Soper, S.A. et al. "Bio-Mems Technologies and Applications", Chapter 12, "MEMS for Drug Delivery", p. 325-346, Date: 2006.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

* cited by examiner

12# IDENTIFIER CIRCUITS FOR GENERATING UNIQUE IDENTIFIABLE INDICATORS AND TECHNIQUES FOR PRODUCING SAME

CROSS-REFERENCE TO RELATED APPLICATIONS

Pursuant to 35 U.S.C. §119 (e), this application claims priority to the filing dates of U.S. Provisional Application Ser. Nos. 61/088,355 filed on Aug. 13, 2008, the disclosures of which are herein incorporated by reference.

BACKGROUND

Ingestible devices that include electronic circuitry have been proposed for use in a variety of different medical applications, including both diagnostic and therapeutic applications.

Examples of such ingestible devices are ingestible electronic capsules which collect data as they pass through the body, and transmit the data to an external receiver system. An example of this type of electronic capsule is disclosed in U.S. Pat. No. 5,604,531 Iddan et al., which describes what is called an in vivo video camera. The swallowable capsule includes a camera system and an optical system for imaging an area of interest onto the camera system. The transmitter transmits the video output of the camera system and the reception system receives the transmitted video output. U.S. Pat. No. 7,009,634 also issued to Iddan et al discloses an ingestible imaging device that obtains images from within body lumens or cavities. The electronic circuit components of the device are enclosed by an inert indigestible housing (e.g. glass housing) that passes through the body internally. U.S. Pat. No. 6,800,060 issued to Marshall discloses an ingestible data recorder capsule medical device. The electronic circuits of the disclosed device (e.g. sensor, recorder, etc.) are housed in a capsule made of inert materials, and therefore ingestible and passable through the digestive tract without being consumed by the body.

In these devices, the electronic circuits are protected in a housing or capsule that prevents damage to the device's electronic circuits during the process of ingestion and elimination in the human body.

Recently, U.S. Patent Application Publication No. 2007/0008113 by Spoonhauer et al. disclosed fragile radio frequency identification (RFID) tags for use in drug ingestion monitoring applications. The RFID tags disclosed in this application are simple antenna structures that are configured to break down during transit through the body.

In certain instances, more complex circuitry suitable for use in ingestible devices is needed.

SUMMARY

The present invention provides for robust ingestible circuitry, where the components of the ingestible circuitry are ingestible, and in some instances digestible. As the ingestible circuitry is made up of ingestible, and even digestible, components, the ingestible circuitry results in little, if any, unwanted side effects, even when employed in chronic situations. The ingestible circuitry is particularly suited for use in signal identifiers, e.g., as may be found in ingestible event markers (IEMs), which include pharma-informatics enabled compositions.

Embodiments of ingestible circuitry of the invention include a solid support of an ingestible material, which support has on a surface thereof one or more electronic components. Components that may be present on the surface of the support may vary, and include but are not limited to: logic and/or memory elements, e.g., in the form of an integrated circuit; a power device, e.g., battery, fuel cell or capacitor; an effector, e.g., sensor, stimulator, etc.; a signal transmission element, e.g., in the form of an antenna, electrode, coil, etc.; a passive element, e.g., an inductor, resistor, etc. The one or more components on the surface of the support may be laid out in any convenient configuration. Where two or more components are present on the surface of the solid support, interconnects may be provided. All of the components and the support of the ingestible circuitry are ingestible, and in certain instances digestible.

DETAILED DESCRIPTION

Figure 1:
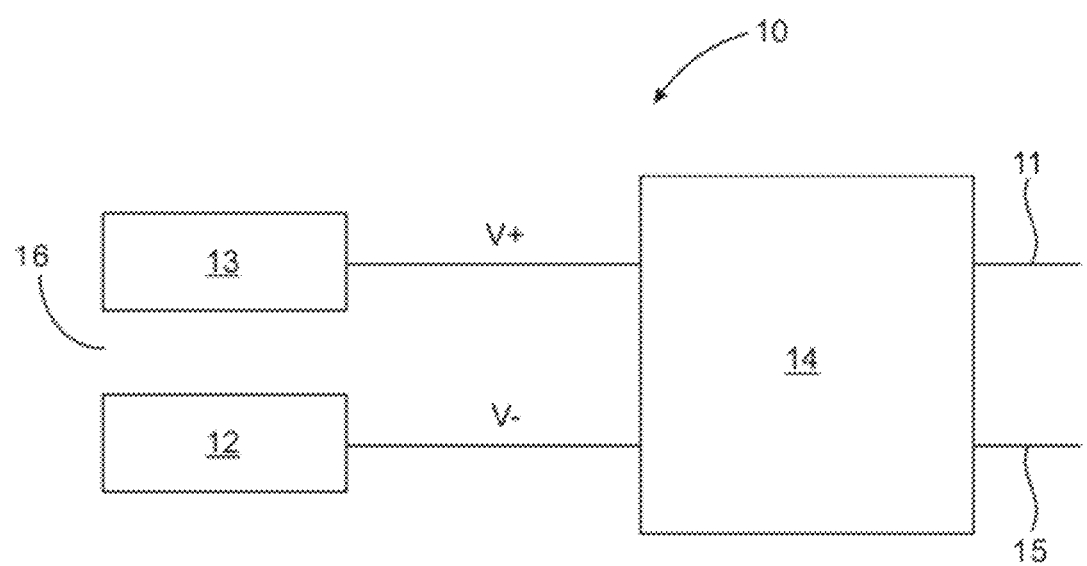
FIG. 1 shows diagrammatically an ingestible identifier that includes ingestible circuitry in accordance with the invention.

The present invention provides for ingestible circuitry, where the components of the circuitry are ingestible, and in some instances digestible. As the ingestible circuitry is made up of ingestible, and even digestible, components, the ingestible circuitry results in little, if any, unwanted side effects, even when employed in chronic situations.

Embodiments of ingestible circuitry of the invention include a solid support of an ingestible material, which support has on a surface thereof one or more electronic components. Components that may be present on the surface of the support may vary, and include but are not limited to: logic and/or memory elements, e.g., in the form of an integrated circuit; a power device, e.g., battery, fuel cell or capacitor; an effector, e.g., sensor, stimulator, etc.; a signal transmission element, e.g., in the form of an antenna, electrode, coil, etc.; a passive element, e.g., an inductor, resistor, etc. The one or more components on the surface of the support may be laid out in any convenient configuration. Where two or more components are present on the surface of the solid support, interconnects may be provided.

The ingestible circuitry is particularly suited for use in signal identifiers, e.g., as may be found in ingestible event markers and pharma-informatics enabled compositions. One example includes use of the ingestible circuitry in association with a specific pharmaceutical product, such as a pill, to determine when a patient takes the pharmaceutical product. As the pill is consumed, the ingestible circuit is activated and generates a signal that is detected thereby signifying that the pharmaceutical product has been taken by a patient.

Ingestible Circuitry and Fabrication Thereof

As summarized above, the present invention provides ingestible circuitry. Ingestible circuitry of the invention includes a solid support fabricated from an ingestible material, and one or more electronic components displayed on a surface thereof. Where two or more components are present on a given solid support, conductive interconnecting elements are also present that electrically couple the two or more components. A variety of different types of components may be present on the support, as reviewed in greater detail below. In addition, one or more optional elements, such as a protective layer, etc., may be provided.

Ingestible circuitry of the invention can be a standalone unit or it can be incorporated into another structure, e.g., an ingestible identifier, such as may be found in an ingestible event marker, including a pharma-informatics enabled pharmaceutical composition.

As summarized above, circuitry of the invention is ingestible, where the disparate components of the circuitry are fabricated from ingestible materials. In certain embodiments, one or more of the ingestible materials of the circuits are digestible materials. As such, the amounts of the materials are below chronic ingestion limits if the circuitry is present in a device that is going to be ingested chronically. If the circuitry is incorporated into a device that is going to be ingested less frequently, materials may be chosen based on the anticipated dosage schedule.

As reviewed above, elements of the ingestible circuitry of the invention include a solid support, one or more electronic components, and interconnects, among other elements.

The solid support is the structure on which all of the components are present. The solid support is fabricated from an ingestible material, where the material is a dielectric or insulating material. It can be fabricated from a variety of materials. Materials that provide mechanical strength and may be employed as an insoluble component of the solid support include, but are not limited to: Ethyl cellulose (e.g. Hercules Aqualon or Dow Ethocel), cellulose acetate, Agar, Gelatin. Insoluble materials of interest include ethylcellulose, a copolymer of acrylic acid and methacrylic acid esters, having from about 5 to 10% functional quaternary ammonium groups, polyethylene, polyamide, polyvinylchloride, polyvinyl acetate and any mixtures thereof. Fillers, such as, starch, glucose, lactose, inorganic salts such as sodium or potassium chloride, carbonates, bicarbonates, sulfates, nitrates, silicates (e.g., magnesium silicate) and alkali metals phosphates and oxides (e.g., titanium dioxide, magnesium oxide), may also be present. Soluble materials that may be employed, e.g., as disintegrating agents, in the solid support include, but are not limited to: Hydroxypropyl cellulose, hydroxyethylcellulose, carboxymethylcellulose, croscarmellose, hypromellose, hydroxypropyl methyl cellulose, methyl cellulose, Polysaccharides (starch, different sugars); Polyvinyl alcohol; Gums (guar, xanthan, acacia); Alginates (sodium or calcium alginate); povidone; etc. Also of interest are Plasticizing agents, e.g., Dibutyl sebacate, triacetin, triethyl citrate, polyethylene glycol, polyethylene oxide. Soluble materials of interest include proteins, polysaccharides, polyacrylates, hydrogels, polyvinyl alcohol, polyvinyl pyrrolidone, and derivatives of such polymers. In certain embodiments, plasticizers may be present, where plasticizers make it easier to process and modulate the strength so that it is not stiff and brittle. Also of interest are surfactants. Environmentally sensitive materials may also be present in the support, such as environmentally sensitive polymers, e.g., temperature sensitive polymers, ph sensitive polymers (e.g., Polymethacrylates (e.g. Degussa Eudragit®)), oxygen sensitive polymers, enzyme sensitive polymers (e.g., Starch, Chitosan, etc.), that will make it insoluble in certain physiological locations, such as the stomach, and soluble in other physiological locations, such as the intestine. Embodiments of such supports are supports that retain their shape in the stomach and then fall apart upon entry/transit through the intestine. Also present may be foaming agents, e.g., sodium carbonate, swelling agents, e.g., hydrogel polymers, or cross linking agents, e.g., glutaraldehyde. In certain embodiments, the support is fabricated from a foodstuff which has suitable properties. Foodstuffs of interest include, but are not limited to: soy, whey, wheat glutein, rice starch, tapioca starch, rice paper, nori, corn chips, potato, pasta, filo, fruit roll-ups, haw flakes, crackers, gelatin and gummy. The solid supports can be fabricated via any convenient protocol, such as through deposition via a number of methods such as solvent cast, or melt extrusion.

Also present in ingestible circuitry is one or more conductive elements which serve to interconnect two or more distinct components on a surface(s) of the support. In certain embodiments, this conductive element, e.g., interconnect or wire, is a thin layer or strip of a homogenous conductive and ingestible material, such as gold, silver, graphite, titanium, copper, etc. The material making up the conductive element may be any material whose total amount is below chronic ingestion limits (i.e., how often one is ingesting the ingestible device) where the conductivity is within a desired range. Table 1 below provides examples of ranges.

TABLE 1

| Metal | Resistivity ($\Omega$m) | Dimension | | |
|---|---|---|---|---|
| | | Length | Width | Thickness |
| Cu | $1.68 \times 10^{-8}$ | 1 cm | 100 µm | 1 µm |
| Mg | $4.39 \times 10^{-8}$ | 1 cm | 100 µm | 10 µm |
| Au | $2.21 \times 10^{-8}$ | 1 cm | 100 µm | 100 µm |
| Ag | $1.59 \times 10^{-8}$ | 1 cm | 10 µm | 1 µm |
| Fe | $9.61 \times 10^{-8}$ | 1 cm | 100 µm | 0.1 µm |

The conductive elements (i.e., interconnects) can be deposited on a surface of the support to provide interconnection between two or more components as a homogeneous layer, for example a layer of gold. Any convenient deposition protocol may be employed, such as but not limited to: evaporation, plating, electrolysis plating, galvanic deposition, screen or ink jet printing, or other thin layer deposition techniques. Alternatively, a lamination method may be employed, where various elements are positioned as sheets. In yet other embodiments, a decal transfer process may be employed, where each of the distinct elements is on a separate backing layer. The distinct elements are transferred to the solid support, and then the backing layer is removed. With each of the above protocols, a patterning technique may be employed. The choice of patterning technique will depend on the choice of deposition process and the dimensional control required of the final pattern, for example evaporation or plating is very compatible with photo lithography. For laminate protocols, laser patterning might be employed, e.g., where a layer is deposited and the unwanted portions are cut out. In certain embodiments, purely additive techniques, such as ink jet or screen printing, are employed.

Instead of having a conductive element fabricated from a homogenous material, the conductive element can be a heterogenous material that is a paste or an ink. For example, a suspension of a conductive filler of the conductive materials, e.g., gold, silver, graphite, etc., with an ingestible binder material, such as a polymer, a thermoset or thermoplastic polymer, may be employed. This heterogenous material can contain other polymeric components such as plasticizers, surfactants to make the ink and the paste flow better, be more processable etc. In yet other embodiments, the conductive element is an isotropic conductive film, e.g., a film of inert particles, such as of a material like glass, that have been coated with a conductive material, e.g., a metal.

Electrical connection between the conductive element and components on the support may be achieved in a number of different ways. For example, interconnects and various components may be positioned on a surface of the solid support, and a layer of conductive material that covers the disparate components and conductive elements can be deposited in a manner that provides the desired connection. Alternatively, ingestible conductive glues, pastes and adhesives may be employed. In certain embodiments, of interest is the use of a combination of two (or more) glues, where one of the glues provides for desired conductive properties and one of the glues provides mechanical strength. In addition, mechanical attachment protocols such as pressing different components together, e.g., where the components have suitable shape interfaces that make it easier for them to bond under mechanical force, pressure, and temperature, may be employed. Also of interest is laser welding, sonic welding, etc. The components can be immobilized relative to a surface of the solid support by mechanically holding the components on to the solid support, e.g., via deposition of a conductive overlay, as reviewed above, by way of a glue, such as a thermoplastic glue that physically holds items in place or thermosetting glue that is cross linked. Lasers may be employed with mixtures of some metals or conductive elements and locally sintered to make an electrical contact at the sintered point (e.g., where the laser removes or densifies an organic material in a binder, leaving a more thermally stable conductive material behind).

In addition to the above components, the ingestible circuitry of the invention also includes one or more electronic components. Electrical components of interest include, but are not limited to: logic and/or memory elements, e.g., in the form of an integrated circuit; a power device, e.g., battery, fuel cell or capacitor; an effector, e.g., sensor, stimulator, etc.; a signal transmission element, e.g., in the form of an antenna, electrode, coil, etc.; a passive element, e.g., an inductor, resistor, etc.

The various components may be produced on a surface of a solid support using a variety of different protocols. For example, where the components are electrode elements that make up a battery which is activated upon contact with stomach fluid, e.g., as described below, the battery components can be deposited directly onto the solid support. For example, a magnesium layer can be evaporated onto a surface of the solid support, where the solid support is fabricated from a material (s) that withstands the temperature and pressure that occurs during that deposition process. The different components of the electrodes can be deposited onto a conductor layer that is then attached to the solid support. For example, one can have a thin sheet of gold, and a layer of CuCl can be deposited onto the gold, with the resultant product being attached to the solid support. The different layers can also be deposited via an ink or a paste. For example, a structure of CuCl deposited on gold can be broken up into small particles, and an ink material can be fabricated from the particles. The resultant ink material can be used to either print or silk screen the desired electrode pattern onto the solid support. Also of interest are protocols that employ screen printing or ink jet printing techniques. In yet other embodiments, an unpatterned slurry is deposited. In yet other embodiments, "roll-to-roll" or "continuous web" protocols are employed.

In certain embodiments, the ingestible circuitry includes a coating layer. The purpose of this coating layer can vary, e.g., to protect the circuitry, the chip and/or the battery, or any components during processing, during storage, or even during ingestion. For example, one may not desire the circuitry to be exposed to the body fluids after it is ingested. In such instances, it may be desirable to only have the battery and transmit antennas be exposed to body fluids, with the rest of the circuitry being protected. In such instances, a coating on top of the circuitry that is ingestible but does not dissolve until the device is finished doing its transmission may be provided. Also of interest are coatings that are designed to protect the ingestible circuitry during storage, but dissolve immediately during use. For example, coatings that dissolve upon contact with an aqueous fluid, e.g., stomach fluid. Also of interest are protective processing coatings that are employed to allow the use of processing steps that would otherwise damage certain components of the device. For example, in embodiments where a chip with battery material deposited on the top and bottom is produced, the product needs to be diced. However, the dicing process can scratch off the battery material, and also there might be liquid involved which would cause the battery materials to discharge or dissolve. In such instances, a protective coating on the battery that prevents mechanical or liquid contact with the battery component during processing can be employed. Another purpose of the edible coatings would be to control the activation of the device. For example, an edible coating that sits on the battery electrodes and takes a certain period of time, e.g., five minutes, to dissolve upon contact with stomach fluid may be employed. The coating can also be an environmentally sensitive coating, e.g., a temperature or pH sensitive coating, or other chemically sensitive coating that provides for dissolution in a controlled fashion and allows one to activate the device when desired. Coatings that survive the stomach but dissolve in the intestine are also of interest, e.g., where one desires to delay activation until the device leaves the stomach. An example of such a coating is a polymer that is insoluble at low pH, but becomes soluble at a higher pH. Also of interest are pharmaceutical formulation protective coatings, e.g., a gel cap liquid protective coating that prevents the circuit from being activated by liquid of the gel cap.

Another component present in certain embodiments of the ingestible circuit is an activation mechanism, e.g., where the activation mechanism is distinct from the power source (e.g., battery). An example of such an alternative activation element is a patch of circuit that closes upon contact with fluid and activates the device. Another example is the reactive removal of a patch of the circuit that, before it is removed, keeps the circuit from operating.

As indicated above, ingestible circuitry devices in accordance with the invention may be fabricated in a variety of different ways. Any of a variety of different protocols may be employed in manufacturing the circuitry structures and components thereof. For example, molding, deposition and material removal, e.g., planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electroplating, cathodic arc deposition, plasma spray, screen or ink jet printing, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, sacrificial lift-off etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in PCT application serial nos. PCT/US2006/016370; PCT/US2007/022257; PCT/US2007/082563; PCT/US2008/052845; PCT/US2008/053999; and PCT/US2008/077753; the disclosures of which are herein incorporated by reference.

In certain embodiments, of interest is a bifurcated laminate process for preparing a device made up of ingestible circuitry. In this bifurcated laminate process, a laminate component is made separate from a circuitry component, allowing greater freedom in terms of processing protocols than may be employed to fabricate the disparate components together, since protocols may be employed to fabricate a first component that cannot be used to fabricate the other, and vice versa. In such bifurcated laminate protocols, the circuitry and laminate components are combined into a single device following separate fabrication of the two components. To combine the two components, any convenient protocol may be employed. In certain embodiments, the circuitry component is fixed into receiving feature of the laminate component, and fixed in place with a suitable adhesive, such as a conductive adhesive. An example of the use of this protocol for the fabrication of an ingestible event marker according to an embodiment of the invention is provided below in connection with a description of FIGS. 7A to 7B.

Figure 7A:
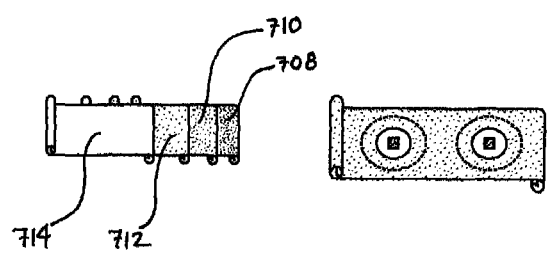
FIGS. 7A to 7B provide views of a bifurcated laminate process employed to fabricate devices according to one embodiment of the invention.

In FIG. 7A, an initial laminate sheet which includes battery elements and a virtual dipole element (e.g., skirt) of an ingestible event marker is shown being prepared using a "continuous web" or "roll-to-roll process". The initial laminate sheet is characterized by having exposed battery layers, e.g., upper and lower exposed battery layers, and includes a first battery layer 708, e.g., CuCl layer (e.g., produced by evaporation, electrodeposition, slurry deposition, silkscreen, or inkjet, etc.), a second virtual dipole layer 710 positioned on top of the battery layer (i.e., skirt), a third current collector layer 712, e.g., Au, Cu, or graphite, etc., which may be a sheet or printed on the skirt, on top of the virtual dipole layer, and a fourth battery layer 714, e.g., Mg foil. Where desired, one or more of the layers can be made separately before lamination, so each process need not be compatible with all the layers e.g., current collector can be graphite-based, made with a high temperature process, which may be incompatible with processes and/or materials used to fabricate the other layers. Layers may be glued together with edible, cellulose adhesive or other safe pressure sensitive adhesives (including but not limited to, silicon materials, etc.).

Fabricated separate from the laminate component is the circuitry component. The circuitry component may be fabricated using any convenient protocol, e.g., as summarized above.

Figure 7B:
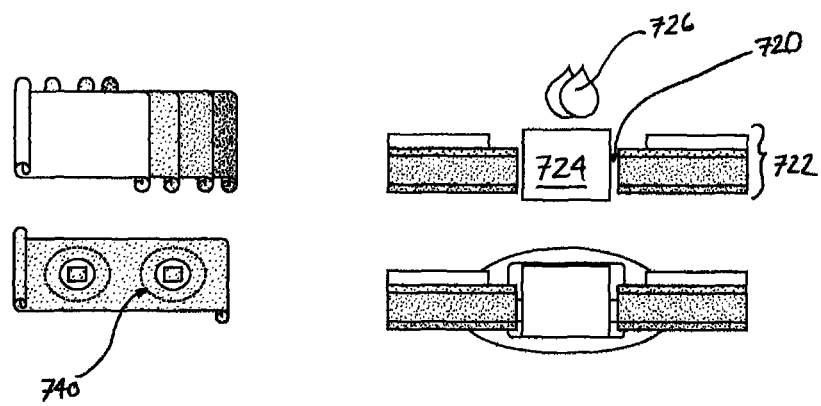

Next, a hole or passage 720 configured to receive the circuitry component (e.g., integrated circuit (IC)) is punched in the resultant laminate component 722 to receive the circuitry component 724, as shown in FIG. 7B. The circuitry component is then positioned in the passageway and fixed in place with a conductive adhesive 726, e.g., as shown in FIG. 7B. A variety of conductive adhesives may be employed, e.g., a polymer filled with conductive particles or a reactive (2-part) glue. The conductivity of the adhesive may be moderate. Where desired, the adhesive can be covered with a final layer of insulating adhesive.

In a variation of the above protocol, a pre-punched lower laminate is employed. In this embodiment, the IC is placed onto a pre-punch hole, where prior to placement, the sheet may be covered with a pressure sensitive adhesive material that is removed prior to chip placement during punching but is removed prior to chip placement. A second laminate is applied over the top of the chips and then opened, e.g., with a laser, over the chips and the top conductor (e.g., battery material) is additively applied, e.g., by screen printing. A final non-conductive layer, such as treated paper or plastic, is used in a roll-to-roll process after this step to isolate the two sides of the battery before the IEMs are finally punched out of the roll for assembly into tablets or capsules.

Finally, a disc shaped device 740, e.g., shown by dashed lines in FIG. 7B, is punched out to produce the desired IEM.

The above bifurcated laminate protocol finds use in, among other applications, fabricating IEMs that have a virtual dipole, e.g., as described in greater detail in pending U.S. Provisional Application Ser. No. 60/975,108 titled "Virtual Dipole Signal Amplification For Pharma-Informatics System" and filed on Sep. 25, 2007, the disclosure of which is herein incorporated by reference.

Devices Comprising Ingestible Circuitry

Ingestible circuitry of the invention finds use in a variety of different types of devices. One example of a device that can include ingestible circuitry of the invention is an ingestible identifier. Ingestible identifiers are described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; PCT application serial no. PCT/US2008/077753 published as WO2009/042812; PCT application serial no. PCT/US2008/085048 published as WO 2009/070773; and PCT application serial no. PCT/US2009/36231; as well as pending U.S. application Ser. Nos. 12/126,792 and 12/126,798; the disclosures of which are incorporated herein by reference.

An example of such an ingestible identifier is an identifier that includes battery. The battery includes, when completed, a cathode, an anode, and an electrolyte, where the electrolyte component is provided by a physiological fluid, e.g., stomach acid. When the identifier is ingested and reaches the stomach, the cathode and anode are exposed to stomach fluid. The stomach fluid (either by itself or when combined with a dried conductive precursor medium component of the identifier, e.g., as described in pending PCT application serial no: PCT/US2007/082563 the disclosure of which is herein incorporated by reference) acts as the electrolyte component of the battery. Completion of the battery powers the circuitry of the identifier which, in turn broadcasts a detectable signal.

Identifiers of interest include two dissimilar electrochemical materials which constitute the two electrodes (e.g., anode and cathode) of the battery. When the electrode materials are exposed and come into contact with the body fluid, such as stomach acid or other types of fluid (either alone or in combination with a dried conductive medium precursor), a potential difference, that is, a voltage, is generated between the electrodes as a result of the respective oxidation and reduction reactions incurred to the two electrode materials. A voltaic cell, or battery, can thereby be produced. Accordingly, in embodiments of the invention, such batteries are configured such that when the two dissimilar materials are exposed to the target site, e.g., the stomach, the digestive tract, etc., during the physical and chemical erosion of the composition in which the signal generation element is present, a voltage is generated. The two dissimilar materials in an electrolyte are at different potentials. As an example, copper and zinc when put into a cell have different potentials. Similarly, gold and magnesium have different potentials. As a result, a potential difference between the two dissimilar materials is generated.

In certain of these embodiments, the battery power source may be viewed as a power source that exploits electrochemical reaction in an ionic solution such as gastric fluid, blood, or other bodily fluids and some tissues. FIG. 1 provides a diagrammatic representation of an ingestible identifier 10 having a battery that is completed by stomach fluid. First and second electrode materials (12 and 13) are present in an ionic solution 16 (which may be made up of target site fluid alone or target site fluid combined with a dried conductive medium precursor). This configuration creates a low voltage (V−) and a high voltage (V+) as applied to corresponding inputs of an electronic circuit 14. The polarity of the electrodes is determined by the connection needs of the electronic circuit 14 and the design as illustrated is just one embodiment. Thus, it will be apparent to one skilled in the art that the scope of the present invention includes reversal of the polarity of the electrodes, such that electrode 13 represents the low voltage and electrode 12 represents high voltage. The two outputs of that electronic circuit 14 are E0 11 and E1 15, which are the signal-transmission electrodes on the top surface.

Electrodes 12 and 13 can be made of any two materials appropriate to the environment in which the identifier 10 will be operating. The active materials are any pair of materials with different electrochemical potentials, as long as they are ingestible, e.g., as described above. For instance, in some embodiments where ionic solution 16 comprises stomach acids, electrodes 12 and 13 may be made of a noble metal (e.g., gold, silver, platinum, palladium or the like) so that they do not corrode prematurely. Suitable materials are not restricted to metals, and in certain embodiments the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to those reported in Table 2 below.

TABLE 2

|  | Anode | Cathode |
|---|---|---|
| Metals | Magnesium, Zinc Sodium (†), Lithium (†) Iron and alloys thereof |  |
| Salts |  | Copper salts: iodide, chloride, bromide, sulfate, formate, (other anions possible) $Fe^{3+}$ salts: e.g. orthophosphate, pyrophosphate, (other anions possible) Oxygen or hydrogen (††) on platinum, gold or other catalytic surfaces |

TABLE 2-continued

|  | Anode | Cathode |
|---|---|---|
| Intercalation compounds | Graphite with Li, K, Ca, Na, Mg | Vanadium oxide Manganese oxide |

(†) Protected anodes: certain high energy anode material such as Li, Na, and other alkali metals are unstable in their pure form in the presence of water or oxygen. These may however be used in an aqueous environment if stabilized. One example of this stabilization is the so-called "protected lithium anode" developed by Polyplus Corporation (Berkeley, CA), where a polymer film is deposited on the surface of lithium metal to protect it from rapid oxidation and allow its use in aqueous environment or air ambient. (Polyplus has IP pending on this).
(††) Dissolved oxygen can also serve as a cathode. In this case, the dissolved oxygen in the bodily fluids would be reduced to OH— at a suitable catalytic surface such at Pt or gold. Also of interest dissolved hydrogen in a hydrogen reduction reaction.

In certain embodiments, one or both of the metals may be doped with a non-metal, e.g., to enhance the voltage output of the battery. Non-metals that may be used as doping agents in certain embodiments include, but are not limited to: sulfur, iodine and the like.

In certain embodiments, the electrode materials are cuprous iodine (CuI) or cuprous chloride as the cathode and magnesium (Mg) metal or magnesium alloy as the anode. Embodiments of the present invention use electrode materials that are not harmful to the human body.

In certain embodiments, the batteries have a small form factor. Batteries may be about 20 $mm^3$ or smaller, e.g., about 10 $mm^3$ or smaller, such as 1.0 $mm^3$ or smaller, including 0.1 $mm^3$ or smaller, including 0.02 $mm^3$ or smaller. In certain embodiments, the battery element is dimensioned to have a width ranging from about 0.01 mm to about 100 mm, e.g., from about 0.1 mm to about 20 mm, including from about 0.5 mm to about 2 mm; a length ranging from about 0.01 mm to about 100 mm, e.g., from about 0.1 mm to about 20 mm, including from about 0.5 mm to about 2 mm, and a height ranging from about 0.01 mm to about 10 mm, e.g., from about 0.05 mm to about 2 mm, including from about 0.1 mm to about 0.5 mm.

The ingestible identifier 10 uses the voltage potential difference to power up electronic circuit 14. In one embodiment, the electronic circuit 14 modulates conductance to create a unique and identifiable current signature.

Figure 2A:
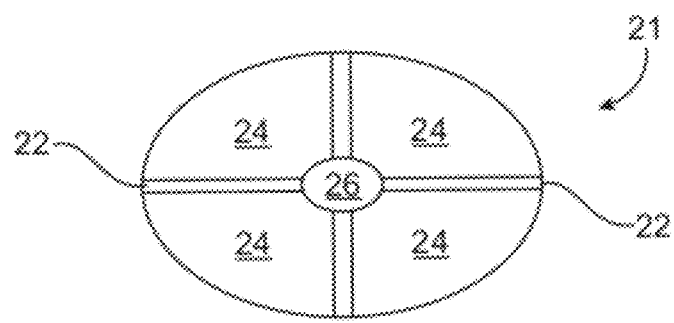
FIGS. 2A to 2D provide views of assembly of an ingestible identifier that includes ingestible circuitry in accordance with the invention.
Figure 2B:
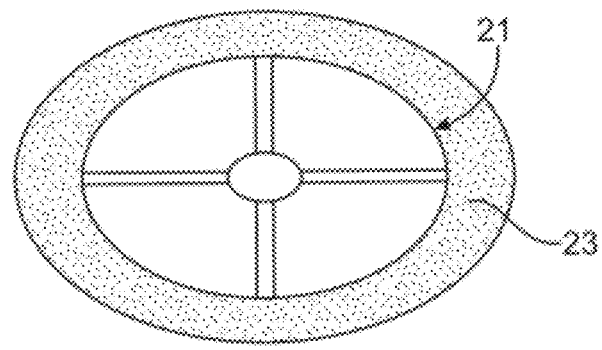
Figure 2C:
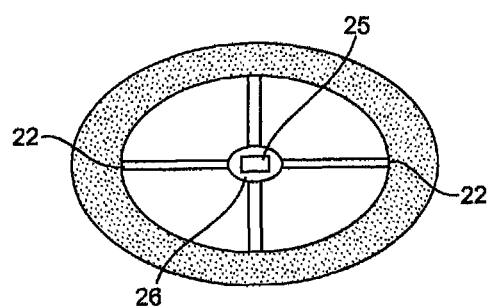
Figure 2D:
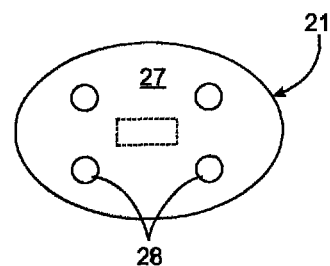

In certain embodiments, the battery has a laminate structure. As indicated above, a laminate process may be employed to fabricate ingestible circuitry in accordance with the invention. An example of such a laminate process is illustrated in FIGS. 2A to 2D. In FIG. 2A, structure 21 is made up of circular metallic foil 22, e.g., gold, and has patterned areas of an electrode material, such as CuCl, patterned on its surface in the form of four distinct quadrants 24. The CuCl regions 24 may be produced on the surface of the foil via any convenient protocol, such as evaporation. Also shown is area 26 which lacks electrode material and is configured to receive an integrated circuit. In FIG. 2B, structure 21 placed onto solid support 23, which support is made of an ingestible material, e.g., as described above. Structure 21 may be placed onto support 23 in a manner such that the two components are stably associated with each other, e.g., by press-fitting the structure 21 onto support 23 or gluing structure 21 onto support 23, among other ways to immobilize structure 21 onto support 23. While the sequence shown in FIGS. 2A and 2B illustrate a protocol in which structure 21 is produced before placement on support 23, in another embodiment the metallic foil 22 is first placed on support 23. Following placement of metallic foil 22 on support 23, the patterned areas of electrode material 24 are produced on the surface of metallic foil 22. In FIG. 2C, integrated circuit 25 is positioned in area 26 and connected to metallic foil 22. Finally, in FIG. 2D, a cover layer 27 (e.g., fabricated from the same material as the support) having electrode cutout areas 28 is stably positioned (e.g., with an ingestible adhesive) over structure 21 to produce a final ingestible circuit device that includes a solid support, an integrated circuit and four distinct surface electrodes. In this structure, the metallic foil layer 22 serves as the conductive interconnect between the different electronic components, i.e., the integrated circuit and electrodes, that are positioned on the surface of the support.

Figure 3A:
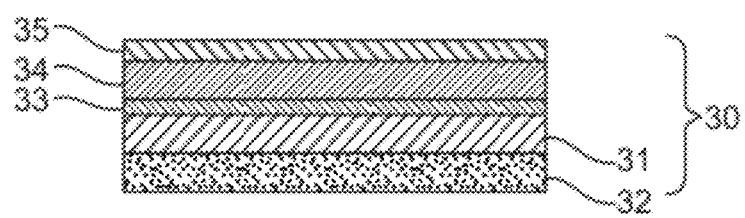
FIGS. 3A and 3B provide views of assembly of an ingestible identifier that includes ingestible circuitry in accordance with the invention.

FIG. 3A illustrates another embodiment of a laminate process that may be employed to construct an ingestible circuit device of the invention. In FIG. 3A, structure 30 has been produced by first providing a release layer 31 on a backing layer 32. Metallic layer (e.g., gold) 33 has been deposited on the surface of release layer 31. Next, electrode material 34, e.g., CuCl, is deposited on surface of metallic layer 33. Finally, insulating layer 35 is positioned over electrode layer 34, which insulating layer may have cutout regions (not shown), e.g., as described in connection with the description of FIGS. 2A to 2D.

Figure 3B:
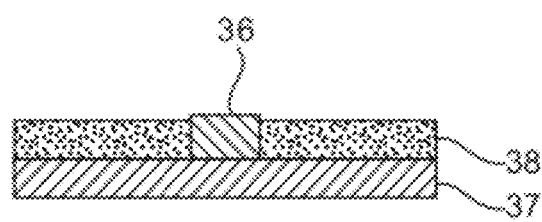

In FIG. 3B, an integrated circuit 36 having a layer of a second electrode material 37, e.g., Mg, on a surface thereof, is positioned in ingestible support 38. To assemble the final device, the release layer 31 and backing layer 32 are removed from structure 30, providing exposed metallic layer 33. This exposed metallic layer 33 is then positioned over circuit 36 and support 38 to yield the final desired device.

Figure 4:
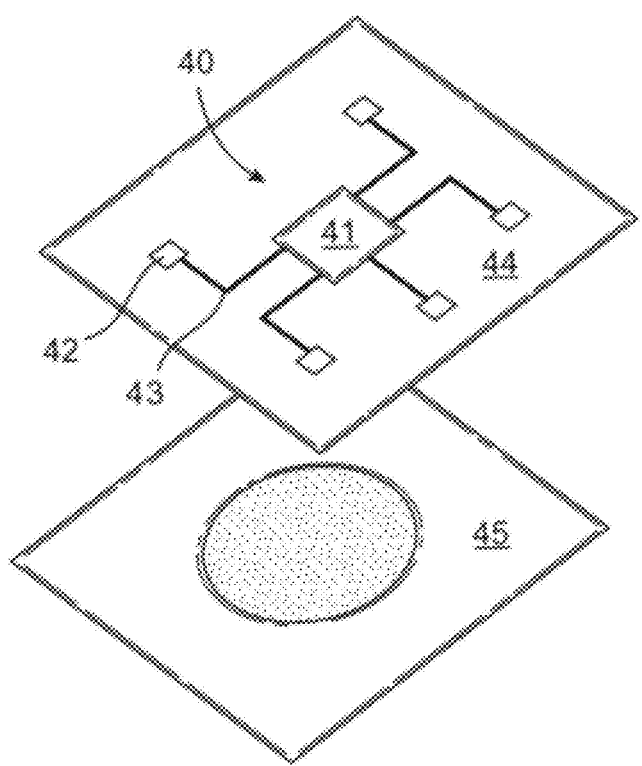
FIG. 4 provides a view of assembly of an ingestible identifier that includes ingestible circuitry in accordance with the invention.

FIG. 4 illustrates a transfer protocol that may be employed to fabricate ingestible circuits in accordance with the invention. In FIG. 4, a circuit structure 40 that includes integrated circuit 41 connected to five different electrodes 42 via interconnecting conductive lines 43 is first produced on a removable backing 44. After production of circuit structure 40, backing 44 is removed and the circuit structure 44 is positioned on the surface of ingestible support 45. The protocol illustrated in FIG. 4 may be employed in processes where parameters of circuit structure production (e.g., chemicals, temperatures, pressures) are incompatible with the solid support material.

Figure 5:
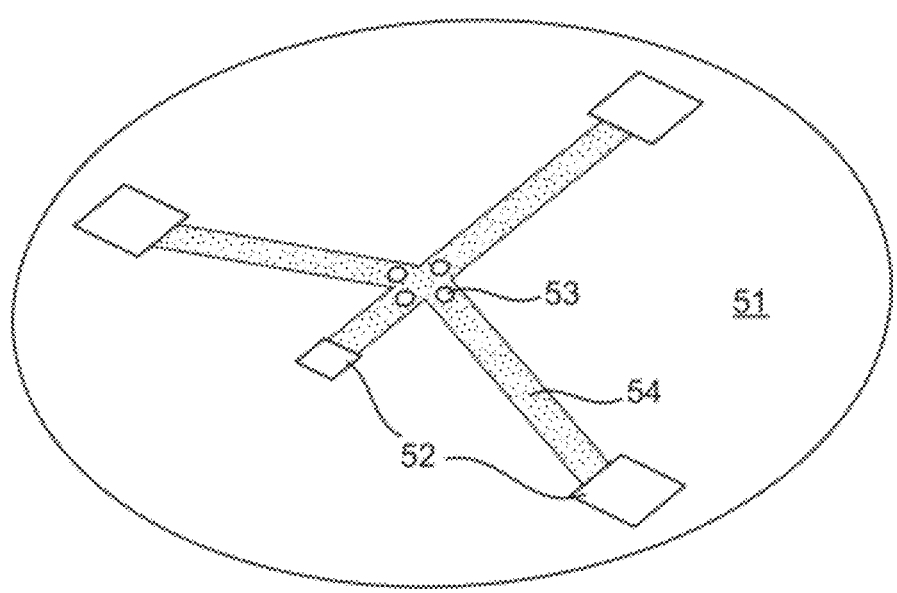
FIG. 5 provides a view of assembly of an ingestible identifier that includes ingestible circuitry in accordance with the invention.

FIG. 5 illustrates a variation in which a conductive ink is employed to provide conductive interconnects between different components of an ingestible circuit device. In the device shown in FIG. 5, ingestible support 51 has displayed on its surface four different electrodes (made up of electrode material) 52. Positioned at a center region of support 51 are four contact pads 53. Interconnecting each electrode to a contact pad is a line of conductive ink material 54. To complete the structure, an integrated circuit is bonded to pads 53 and then a layer of protection material is positioned over the surface leaving exposed electrode elements, analogous to that shown in FIG. 2D.

Figure 6A:
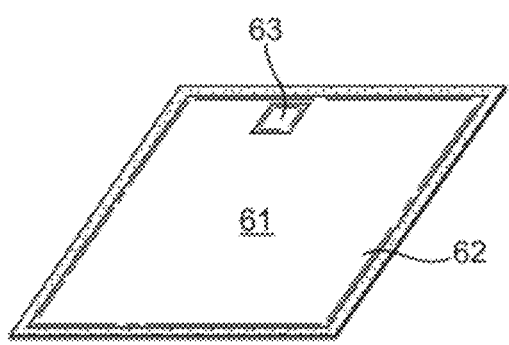
FIGS. 6A and 6B provide views of assembly of an ingestible identifier that includes ingestible circuitry in accordance with the invention.
Figure 6B:
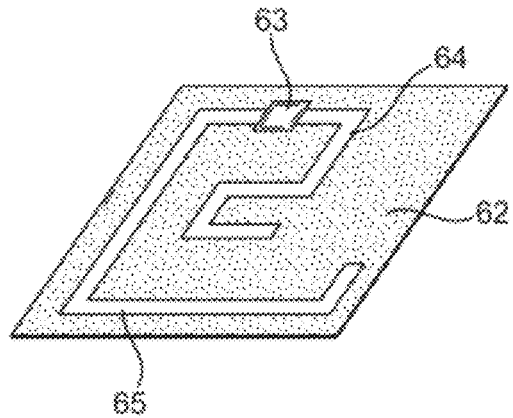

In certain instances, laser patterning may be employed during fabrication of ingestible circuits of the invention, e.g., as illustrated in FIGS. 6A and 6B. In FIG. 6A, a blanket (i.e., non-patterned) layer of metal 61 is deposited on a surface of an ingestible support 62. Positioned on a portion of metal layer 61 is integrated circuit 63. Next, laser patterning is employed to remove portions of metal layer 61 to produce antenna structure 64 and 65 on surface of support 62.

Ingestible identifiers that include ingestible circuitry of the invention find use in a variety of different applications. One application of interest is the use of the ingestible identifiers as ingestible event markers (IEMs). Ingestible event markers can be used in both therapeutic and non-therapeutic applications, and are described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; PCT application serial no. PCT/US2008/077753 published as WO 2009/042812; PCT application serial no. PCT/US2008/085048 published as WO 2009/070773; and PCT application serial no. PCT/US2009/36231; as well as pending U.S. application Ser. Nos. 12/126,792 and 12/126,798; the disclosures of which are incorporated herein by reference.

The disclosure of these ingestible event markers and applications for the same therein is specifically incorporated herein by reference. Therapeutic applications of ingestible identifiers are embodiments where, at least in some instances, the identifier is associated with a pharmaceutical composition. Medical embodiments of the present invention provide the clinician an important new tool in their therapeutic armamentarium: automatic detection and identification of pharmaceutical agents actually delivered into the body. The applications of this new information device and system are multifold. Applications include, but are not limited to: (1) monitoring patient compliance with prescribed therapeutic regimens; (2) tailoring therapeutic regimens based on patient compliance; (3) monitoring patient compliance in clinical trials; (4) monitoring usage of controlled substances; and the like. Each of these different illustrative applications is reviewed in greater detail in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; PCT application serial no. PCT/US2008/077753 published as WO2009/042812; PCT application serial no. PCT/US2008/085048 published as WO 2009/070773; and PCT application serial no. PCT/US2009/36231; as well as pending U.S. application Ser. Nos. 12/126,792 and 12/126,798; the disclosures of which are incorporated herein by reference.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing an identifier, the method comprising:
   laminating a non-conducting element between first and second dissimilar materials to create a laminate component, wherein the first and second dissimilar materials generate a voltage potential when in contact with a conducting fluid;
   removing a portion of the first and second dissimilar materials from the perimeter of the laminate component to expose the non-conducting element and to create a skirt; and
   securing a circuit within an aperture formed in the laminate component, wherein the circuit is electrically coupled to each of the first and second dissimilar materials, and wherein the circuit is operable by the voltage potential generated by the first and second dissimilar materials.

2. The method of claim 1, further comprising selecting the first and second dissimilar materials to create a voltaic cell through oxidation and reduction reactions when the first and second dissimilar materials are in contact with the conducting fluid.

3. The method of claim 2, further comprising configuring the circuit to generate a detectable signal that identifies unique information associated with the identifier.

4. The method of claim 2, wherein the conducting fluid is a physiological fluid.

5. The method of claim 1, further comprising securing the identifier to a pharmaceutical product to produce a tagged product such that activation of the circuit is an indication that the pharmaceutical product of the tagged product is in contact with physiological fluid.

6. The method of claim 5, further comprising sealing the tagged product with a coating to isolate the tagged product from the physiological fluid for a predefined period of time until the coating is dissolved by the physiological fluid to allow the tagged product to reach a target site at which time the tagged product is exposed to the physiological fluid.

7. The method of claim 1, further comprising laminating a current collector element between the non-conducting element and at least one of the first and second dissimilar materials.

8. The method of claim 1, further comprising forming the aperture through the laminate component to receive the circuit within the aperture.

9. The method of claim 1, further comprising fixing the circuit within the aperture with a conductive adhesive.

10. The method of claim 1, further comprising removing a portion of the laminate component encompassing the circuit to produce the identifier.

* * * * *